US012364711B1

(12) United States Patent
Omran et al.

(10) Patent No.: US 12,364,711 B1
(45) Date of Patent: Jul. 22, 2025

(54) INHIBITION OF CANCER CELL VIABILITY

(71) Applicant: IMAM MOHAMMAD IBN SAUD ISLAMIC UNIVERSITY, Riyadh (SA)

(72) Inventors: Mohamed Khairy Abdel Fattah Omran, Riyadh (SA); Babiker Yagoub Elhadi Abdulkhair, Riyadh (SA)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 19/076,524

(22) Filed: Mar. 11, 2025

(51) Int. Cl.
  *A61K 33/00* (2006.01)
  *A61K 33/08* (2006.01)
  *A61K 33/32* (2006.01)
  *A61P 35/00* (2006.01)

(52) U.S. Cl.
  CPC .............. *A61K 33/00* (2013.01); *A61K 33/08* (2013.01); *A61K 33/32* (2013.01); *A61P 35/00* (2018.01)

(58) Field of Classification Search
  CPC ........ A61K 33/00; A61K 33/08; A61K 33/32; A61P 35/00
  See application file for complete search history.

(56) References Cited

U.S. PATENT DOCUMENTS

2023/0149548 A1   5/2023   Yang et al.

FOREIGN PATENT DOCUMENTS

| CN | 104287479 B | 6/2016 |
| CN | 114177289 B | 10/2023 |
| IN | 202311022975 | 10/2024 |

OTHER PUBLICATIONS

Nitha et al. (Journal of Physics: Conference Series 2024; 2801:7 pages) (Year: 2024).*
Salmasi et al. (Applied Surface Science 2022;585:16 pages) (Year: 2022).*
S. Kumaraguru, et al.. "Design and development of CuQ—ZnO nanospheres decorated g-C3N4 nanocomposite with superior antimicrobial and anticancer activities", Biomass Conversion and Biorefinery, vol. 13, 2023, pp. 16227-16239 (13 pages).

* cited by examiner

*Primary Examiner* — Ernst V Arnold
(74) *Attorney, Agent, or Firm* — Oblon, McClelland, Maier & Neustadt, L.L.P.

(57) ABSTRACT

A method of inhibiting cancer cell viability may include contacting cancer cells and a nanocomposite including graphitic $C_3N_4$, $MnO_2$, and $MgAl_2O_4$ in a mass relationship to each other in a range of from 5 to 15:2 to 7:75 to 95, the nanocomposite being at a concentration in a range of from 10.0 to 500 μg/mL, thereby inhibiting the growth of the cancer cells by at least 85%.

20 Claims, 6 Drawing Sheets

INHIBITION OF CANCER CELL VIABILITY

BACKGROUND

Technical Field

The present disclosure is directed towards nanocomposites as anti-cancer agents, and more particularly, relates to a method of inhibiting cancer cell viability using a nanocomposite including graphitic—$C_3N_4$, $MnO_2$, and $MgAl_2O_4$.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Worldwide, cancer remains a leading cause of death and disability due to a complex pathological process associated with a plurality of cancers. Conventional chemotherapy faces several challenges, including cytotoxicity, low therapeutic indices, low bioavailability, insolubility, high dose requirements, non-specific targeting, and the development of multiple drug resistance. Resistance to cancer treatment arises from various factors such as overexpression of drug efflux transporters, anoxic conditions, and abnormal apoptotic pathways. The aforementioned limitations necessitate the exploration of innovative approaches to improve cancer treatment efficacy and patient outcomes.

Nanomaterials (NMs) have emerged as promising anti-cancer agents to address the limitations of conventional chemotherapy. The optimization of NMs in terms of size, shape, and surface characteristics enhances targeting efficiency and prolongs circulation time, thereby increasing the targeting potential of anticancer cargos. NMs may enhance therapeutic efficacy through controlled release mechanisms by encapsulating or coupling therapeutic cargos with ligands, providing precise delivery to cancer sites. In cancer treatment, NMs are employed to target cancer cells, the tumor microenvironment, and the immune system through stimuli-responsive targeting or surface modification with targeting ligands such as transferrin, integrins, sugar, folic acid, and antibodies. The aforementioned functionalization may improve tissue targeting, recognition, and internalization, offering a more effective therapeutic approach. The biomedical applications of NMs are extensive, with their ability to transport ligands and therapeutic compounds or to target cancer cells and tissues through passive, active, or physical targeting methods. The above-described advancements aim to achieve stronger inhibitory therapeutic efficacies in the fight against cancer.

Research in this regard has been conducted, e.g., in *J. Drug Deliv. Therap.* 2023, 13 (12), 201-223, and *Zeitschr. anorg. allg. Chem.* 2021, 647 (19), 1921-1929, each of which is incorporated by reference herein. Despite certain improved therapeutic methods, the application of nanomaterials in cancer treatment faces several challenges and limitations. Key drawbacks include potential toxicity and long-term biocompatibility concerns, difficulties in large-scale production with consistent quality, and challenges in achieving efficient clearance from the body to avoid accumulation and adverse side effects. Additionally, regulatory and clinical translation hurdles pose significant challenges, requiring extensive preclinical and clinical validation to ensure safety and efficacy. The cost of developing and deploying nanomaterial-based therapies is yet another barrier to widespread clinical adoption.

Accordingly, one object of the present disclosure is to provide a method of inhibiting cancer cell viability that may circumvent the above-listed drawbacks and limitations of the methods known in the art.

SUMMARY

The method of inhibiting cancer cell viability may include contacting cancer cells and a nanocomposite including graphitic $C_3N_4$, $MnO_2$, and $MgAl_2O_4$ in a mass relationship to each other in a range of from 5 to 15:2 to 7:75 to 95, the nanocomposite being at a concentration in a range of from 10.0 to 500 μg/mL, thereby inhibiting the growth of the cancer cells by at least 85%.

The average pore distribution of the nanocomposite may be unimodal. The (Brunauer-Emmett-Teller) BET specific surface area of the nanocomposite may be in a range of from 16.2 $m^2/g$ to 20.2 $m^2/g$ (e.g., 18.7 $m^2/g$). The average pore diameter of the nanocomposite, according to (Barrett-Joyner-Halenda) BJH measurement method, may be in a range of 5 to 15 nanometers (nm) (e.g., 8.34 nm). The average pore volume of the nanocomposite, according to the BJH measurement method, may be in a range of from 0.025 $cm^3/g$ to 0.075 $cm^3/g$ (e.g., 0.05 $cm^3/g$).

The nanocomposite may have a (220) spinel interplanar spacing in a range of from 0.258 to 0.338 nm (0.298 nm), (400) spinel interplanar spacing in a range of from 0.165 to 0.245 nm (0.205 nm), (002) $MnO_2$ interplanar spacing in a range of from 0.106 to 0.186 nm (0.146 nm), and (211) $Al_2O_3$ interplanar spacing in a range of from 0.093 to 0.173 nm (0.133 nm), according to selected area diffraction (SAED).

The mass relationship of the nanocomposite may be in a range of from 9 to 11:4 to 6:84 to 86, where the nanocomposite may have a (220) spinel interplanar spacing of 0.298±2% nm, (400) spinel interplanar spacing of 0.205±2% nm, (002) $MnO_2$ interplanar spacing of 0.146±2% nm, and (211) $Al_2O_3$ interplanar spacing of 0.133±2% nm, according to SAED. An X-ray diffraction (XRD) spectrum of the nanocomposite under Cu-filtered Cu-Kα radiation (1.5418 Å) powered at 45 kV and 10 mA may have 20 peaks of an $MnO_2$ pyrolusite phase at 28.4±1°, 40.5±1°, 44.9±1°, 56.0±1°, 66.4±1°, and/or 79.1±1°, an $MgAl_2O_4$ spinel phase at 19.1±1°, 31.3±1°, 44.8±1°, 56.1±1°, 59.5±1°, 74.09±1°, and/or 78.1±1°, an MgO cubic phase at 42.8±1°, 62.2±1°, and/or 74.6±1°, an $Al_2O_3$ phase at 31.3±1°, 34.3±1°, and/or 61.6±1°, and/or g-$C_3N_4$-related diffractions at 18.8±1°, 28.2±1°, 35.5±1°, 40.7±1°, 44.6±1°, and/or 73.7±1°, and no more than 5% relative intensity of any other phase may be detected in the XRD spectrum.

The cancer cells are HepG-2 human hepatocellular carcinoma cells and the concentration of the nanocomposite in the contacting may be in a range of from 75 to 350 μg/mL ($IC_{50}$ against the HepG-2 human hepatocellular carcinoma cells may be 96.56 10, 5, 4, 3.33, 2.5, 2, 1.5, 1, 0.75, 0.67, 0.5, 0.33, 0.25, 0.125, 0.1, 0.05, or 0.01 μg/mL), or the cancer cells are MCF-7 human breast carcinoma cancer cells and the concentration of the nanocomposite may be in a range of from 100 to 450 μg/mL ($IC_{50}$ against the MCF-7 human breast carcinoma cancer cells may be 119.78±25, 15, 10, 5, 4, 3.33, 2.5, 2, 1.5, 1, 0.75, 0.67, 0.5, 0.33, 0.25, 0.125, 0.1, 0.05, or 0.01 μg/mL).

The nanocomposite may have no more than 0.1 parts, individually, of thiol, amine, carboxylate, and hydroxyl functionalization per 100 $MnO_2$ units, relative to a total metal oxide weight.

The nanocomposite may include no more than 1 wt. %, individually or in any combination, of $TiO_2$, $Ti_2AlN$, $Fe_3O_4$, AlN, ZnO, and/or $SiO_2$, relative to a total metal oxide weight.

The nanocomposite may include no more than 1 atoms of Ce, relative to 100 atoms of Mn.

The carbon materials in the nanocomposite include no more than 1 wt. %, individually, carbon nanotubes or carbon dots, relative to total nanocomposite weight.

The nanocomposite no more than 1 wt. % AgBr, relative to a total metal oxide weight. The nanocomposite may be no more than 1 wt. % tungsten oxide, relative to a total nanocomposite weight.

The nanocomposite may include no more than 1 wt. % CuS, relative to total nanocomposite weight.

The nanocomposite may include no more than 1 wt. %, individually or in any combination, CuO, aluminosilicate, and/or WO3, relative to total nanocomposite weight.

The nanocomposite may include no more than 1 wt. %, individually or in combination, elemental state Co and Fe, relative to total nanocomposite weight.

The nanocomposite may include no more than 0.1 wt. % of any noble metal (or all), relative to total nanocomposite weight.

The nanocomposite may include no more than 10 wt. % MgO, relative to a total metal oxide weight, and the nanocomposite may include no clay.

The nanocomposite may include no more than 1 wt. % carbonaceous material besides the graphitic carbon nitride, the graphitic $C_3N_4$ may not be nitrogen deficient, and carbon materials in the nanocomposite include no more than 0.01 wt. % nanotubes and/or nanorods (or none of either or both), relative to total nanocomposite weight.

The nanocomposite may include no more than 10 wt. % $Mn_3O_4$, relative to total manganese oxide weight, and the nanocomposite may include no more than 1 wt. % V-doped ZnO, relative to total nanocomposite weight.

Relative to a total metal oxide weight, the nanocomposite may include no more than 1 wt. %, individually or in any combination, of $Al_2O_3$, ZnO, $Fe_3O_4$, $CeFeO_3$, $GdFeO_3$, $LaFeO_3$, $BaTiO_3$, $CaTiO_3$, $SrTiO_3$, $CaZrO_3$, $PbTiO_3$, $Mg_{1-x}Ni_xFe_2O_4$ (x=0.0, 0.6, 1.0), Ag, $CoFe_2O_4$, $CuFe_2O_4$, $MnFe_2O_4$, $NiFe_2O_4$, $ZnFe_2O_4$, $Cu_{1-x}Cd_xFe_2O_4$, $Zn_{0.7}Ni_{0.15}Cu_{0.15}Fe_2O_4$, $Zn_{0.3}Ni_{0.7-x}Co_xFe_2O_4$ (0≤x≤0.7), $Mn_{0.1}Mg_{0.2}(Co, Ni, Zn)_{0.7}Fe_2O_4$, $LaCo_{0.5}Fe_{0.5}O_3$, $Mg_{0.1}$—$Co_{0.9}Fe_2O_4$, $La_{1-x}Gd_xCr_{1-y}Ni_yO_3$, $Gd_2FeCrO_6$, $KTaO_3$, $NaTaO_3$, $NaNbO_3$, $KNbO_3$, $Mg_{1-x}Ni_xFe_2O_4$, $Cu_{0.5}Cd_{0.25}Co_{0.25}Fe_{2-x}O_4$, $Zn_{0.5}Co_{0.5}La_xFe_{2-x}O_4$, $Pr_2Ti_2O_7$, $SiO_2$, $TiO_2$, ZnS, $Bi_4O_5I_2$, $SrFe_{0.5}Ta_{0.5}O_3$, $La_{0.8}Ba_{0.2}TiO_{3.5-δ}$, $LaTiO_{3.5-δ}$, $NaNbO_3$, and/or $LaFeO_3$.

The graphitic $C_3N_4$ in the nanocomposite may consist essentially of sheet morphologies, i.e., such that no more of 5% of the cell viability inhibitive effectiveness is lost relative to a pure sheet morphology nanocomposite. The graphitic $C_3N_4$ in the nanocomposite may include no more than inevitable traces of boron, e.g., no more than 5, 4, 3, 2.5, 2, 1, 0.5, 0.1, 0.01, 0.001, 0.0001, or 0.00001 wt. %, relative to total nanocomposite weight or total carbonaceous weight of the nanocomposite, of boron.

The nanocomposite may include no more than 10 wt. %, individually or in any combination, relative to total metal content, of any of Zn, Ce, Gd, La, Ba, Ti, Ca, Sr, Zr, Pb, Ni, Ag, Co, Cu, Mn, Cd, W, Ta, Nb, Pr, and/or Bi, and the nanocomposite may include no more than 1 wt. %, individually or in any combination, relative to total carrier weight, of $SiO_2$, $TiO_2$, ZnO, and/or ZnS.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
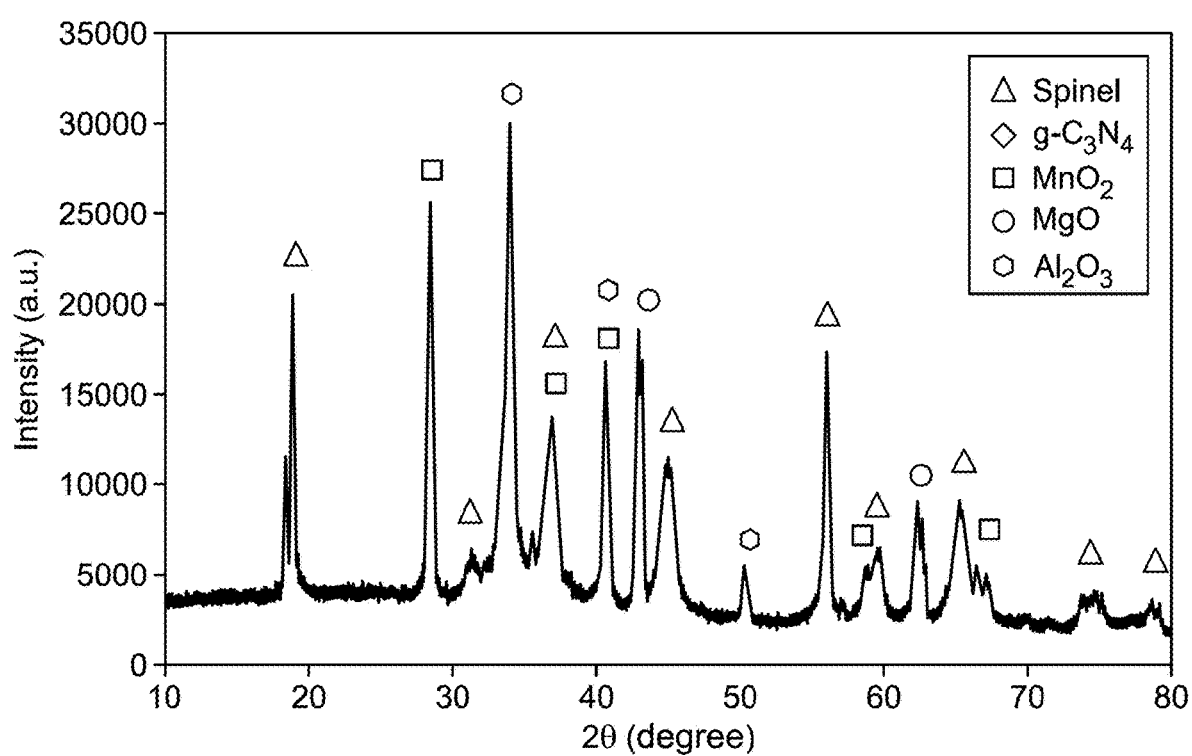
FIG. 1 is a graph depicting X-ray diffraction (XRD) patterns of an inventive g-$C_3N_4$@$MnO_2$/$MgAl_2O_4$ nanocomposite.

When describing the present disclosure, the terms used are to be construed in accordance with the following definitions, unless a context dictates otherwise.

Embodiments of the present invention will now be described more fully hereinafter with reference to the accompanying drawings wherever applicable, in that some, but not all, embodiments of the disclosure are shown.

In the drawings, like reference numerals designate identical or corresponding parts throughout the several views. Further, as used herein, the words 'a,' 'an' and the like generally carry a meaning of 'one or more,' unless stated otherwise.

Furthermore, the terms 'approximately,' 'approximate,' 'about,' and similar terms generally refer to ranges that include the identified value within a margin of 20%, 10%, or preferably 5%, and any values therebetween.

As used herein, the term 'cancer' refers to all types of cancer, neoplasm or malignant tumors found in mammals (e.g., humans), including leukemias, lymphomas, carcinomas, and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

As used herein, the term 'cell viability' refers to the proportion of live, healthy cells in a population after being exposed to various conditions or treatments. It is commonly measured to assess the health and functionality of cells in laboratory studies, particularly when testing the effects of drugs, toxins, or other experimental variables. Viable cells can maintain their metabolism, growth, and division processes, while non-viable cells are damaged, dysfunctional, or dead. Cell viability is often assessed using assays that measure metabolic activity, membrane integrity, or other indicators of cellular health.

As used herein, the terms 'treat,' 'treatment,' and 'treating' in the context of the administration of a therapy to a subject in need thereof refer to the reduction or inhibition of the progression and or duration of cancer, the reduction or amelioration of the severity of cancer, and/or the amelioration of one or more symptoms thereof resulting from the administration of one or more therapies. The subject may be a mammalian subject. The subject may be a human. 'Treating' or 'treatment' of a disease includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer or hyperplasia, these terms simply mean that the life expectancy of an individual affected with cancer will be increased or that one or more of the symptoms of the disease will be reduced. Such terms may refer to one, two or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor may be maintained and does not increase or increases by less than 10%, preferably less than 5%, preferably less than 4%, preferably less than 2%, and (12) an increase in the number of patients in remission. Such terms may refer to a stabilization or reduction in cancer stem cell population. Such terms may refer to a stabilization or reduction in the growth of cancer cells. Such terms may refer to stabilization or reduction in cancer stem cell population and a reduction in the cancer cell population. Such terms may refer to a stabilization or reduction in the growth and or formation of a tumor. Such terms may refer to the eradication, removal, or control of primary, regional, or metastatic cancer (e.g., the minimization or delay of the spread of cancer). Such terms may refer to a reduction in mortality and/or an increase in the survival rate of a patient population. Such terms may refer to an increase in the response rate, the durability of response, or the number of patients who respond or are in remission. Such terms may refer to a decrease in the hospitalization rate of a patient population and/or a decrease in hospitalization length for a patient population.

As used herein, the term 'pharmaceutical composition' refers to a mixture of the compounds described herein or pharmaceutically acceptable salts, esters, or prodrugs thereof, with other chemical components, such as physiologically acceptable carriers and excipients. As used herein, the term 'administering' means oral administration, administration as a suppository, topical contact, intravenous, parenteral, intraperitoneal, intramuscular, intralesional, intrathecal, intranasal, or subcutaneous administration, or the implantation of a slow-release device, e.g., a mini-osmotic pump, to a subject. Administration may be by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. The administering may not include administration of any active agent other than the recited active agent. The administration of the anticancer compound may be selected from a group consisting of intravenous, intraperitoneal, intramuscular, and oral administration.

As used herein, the terms 'anticancer agent' or 'anticancer compound' refer to a molecule (e.g., compound, peptide, protein, nucleic acid, 0103) used to treat cancer through the destruction or inhibition of cancer cells or tissues. Anticancer agents may be selective for certain cancers or certain tissues.

As used herein, the term 'anti-cancer agent' and 'anticancer agent' or 'anticancer compound' are used in accordance with their plain ordinary meaning and refers to a composition (e.g., compound, drug, antagonist, inhibitor, modulator) having antineoplastic properties or the ability to inhibit the growth or proliferation of cells. The anti-cancer agent may be chemotherapeutic. The anti-cancer agent may be an agent identified herein having utility in methods of treating cancer. The anti-cancer agent may be an agent approved by the FDA or similar regulatory agency of a country other than the USA, for treating cancer. Examples of anti-cancer agents include, but are not limited to, MEK (e.g., MEK1, MEK2, or MEK1 and MEK2) inhibitors (e.g., XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g., U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide;

rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g., Taxol™ (i.e. paclitaxel), Taxotere™, compounds including the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g., Altorhyrtin A and Altorhyrtin C), Spongistatins (e.g., Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g., Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (*Asta Medica*), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Caribaeolin, Halichondrin B, D-64131 (*Asta Medica*), D-68144 (*Asta Medica*), Diazonamide A, A-293620 (Abbott), NPI-2350 (*Nereus*), Taccalonolide A, TUB-245 (Aventis), A-259754 (Abbott), Diozostatin, (–)-Phenylahistin (i.e. NSCL-96F037), D-68838 (*Asta Medica*), D-68836 (*Asta Medica*), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), immunotherapy (e.g., cellular immunotherapy, antibody therapy, cytokine therapy, combination immunotherapy, etc.), radioimmunotherapy (e.g., anti-CD20 monoclonal antibody conjugated to 111 In, 90Y, or 1311, etc.), immune checkpoint inhibitors (e.g., CTLA4 blockade, PD-1 inhibitors, PD-L1 inhibitors, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g., gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

As used herein, the term 'nanoparticles (NPs)' refers to particles having a particle size of 1 nanometer (nm) to 500 nm within the scope of the present disclosure.

As used herein, the term 'nanocomposite' is a material that is made by combining a matrix (often a polymer, metal, or ceramic) with NPs or nanomaterials to enhance its properties. The NPs are typically on the scale of nm (e.g., 1 to 100 nm), and their small size and high surface area can significantly improve the strength, thermal stability, electrical conductivity, optical properties, and other characteristics of composite material.

As used herein, the term 'unimodal' refers to a distribution or pattern that has a single peak or mode. In the context of particle size or material properties, it indicates that the sample consists of particles or components that are primarily of one size or characteristic, rather than varying widely in size or composition.

As used herein, the term 'half maximal inhibitory concentration ($IC_{50}$)' refers to the measure of the potency of a substance in inhibiting a specific biological or biochemical function. $IC_{50}$ is a quantitative measure that indicates how much of a particular inhibitory substance (e.g., drug) is needed to inhibit, in vitro, a given biological process or biological component by 50%. The biological component can be an enzyme, cell, cell receptor or microorganism. $IC_{50}$ values are typically expressed as molar concentration.

As used herein, the term 'pore volume' refers to the total volume of void spaces (pores) within a material that are capable of being filled by a gas or liquid. It is typically expressed in cubic centimeters per gram ($cm^3/g$) and is an important parameter in characterizing the porous structure of materials, such as adsorbents or catalysts.

As used herein, the term 'pore diameter' refers to the average width or size of the pores (void spaces) within a material, typically measured in nm or angstroms (Å). It is a key parameter in characterizing the texture and permeability of porous materials, influencing their adsorption, filtration, or catalytic properties. Pore diameter is often determined using methods such as nitrogen ($N_2$) adsorption or mercury intrusion, which provide insights into the material's ability to absorb or interact with molecules of specific sizes.

As used herein, the term 'spinel interplanar spacing' refers to the distance between parallel planes of atoms in the crystal structure of a spinel material. Spinel is a type of mineral with a specific crystalline arrangement, represented by the general formula $AB_2O_4$, where 'A' and 'B' are metal ions. The interplanar spacing is crucial for understanding the material's structural properties and is typically measured using X-ray diffraction (XRD) techniques.

As used herein, the term 'HepG-2 human hepatocellular carcinoma cells' refer to a type of cancer cell line derived from a liver tumor in a human patient.

As used herein, the term 'MCF-7 human breast carcinoma cells' refer to cell line derived from a breast cancer tumor.

As used herein, the term 'antiproliferation agent' refers to a compound or material that inhibits or prevents the proliferation (growth and reproduction) of cells, particularly cancerous or abnormal cells. The antiproliferative effect is achieved through various mechanisms, such as interference with cell cycle progression, induction of apoptosis (programmed cell death), inhibition of DNA/RNA synthesis, or disruption of metabolic pathways essential for cell growth. Antiproliferation agents are generally used in therapeutic applications to target and control the uncontrolled cell division characteristic of cancer and other proliferative disorders.

A weight percent of a component, unless specifically stated to the contrary, is based on the total weight of the formulation or composition in which the component is included. For example, if a particular element or component in a composition or article is said to have 5 wt. %, it is understood that this percentage is in relation to a total compositional percentage of 100%.

The present disclosure is intended to include all hydration states of a given compound or formula, unless otherwise noted or when heating a material.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium, and isotopes of carbon include $^{13}C$ and $^{14}C$. Isotopes of oxygen include $^{16}O$, $^{17}O$, and $^{18}O$ and isotopes of cobalt (Co) are $^{56}Co$, $^{57}Co$, $^{58}Co$, and $^{60}Co$. Isotopes of iron include $^{54}Fe$, $^{56}Fe$, $^{57}Fe$, and $^{58}Fe$. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

Aspects of the present disclosure are directed towards a nanocomposite of graphitic carbon nitride (g-$C_3N_4$), manganese dioxide ($MnO_2$), and magnesium aluminate ($MgAl_2O_4$) (g-$C_3N_4$@$MnO_2$/$MgAl_2O_4$) as an anticancer agent. The nanocomposite may be designed as an anticancer agent, demonstrating effective cytotoxicity against human breast carcinoma (MCF-7) and hepatocellular carcinoma (HepG-2) cell lines.

A nanocomposite (g-$C_3N_4$@$MnO_2$/$MgAl_2O_4$) including g-$C_3N_4$, $MnO_2$, and $MgAl_2O_4$ is described. The g-$C_3N_4$, $MnO_2$, and $MgAl_2O_4$ are present in the nanocomposite in a mass relationship to each other in a range of from 5 to 15:2 to 7:75 to 95, preferably 7 to 13:3 to 6:80 to 90, preferably 9 to 11:4 to 5:84 to 86, and yet more preferably 10:5:85, while tolerable variations of any of these values may be ±2.5, 2, 1.5, 1, 0.75, 0.5, 0.25, 0.1, 0.5, or 0.1.

The nanocomposite may have no more than 0.1, 0.075, 0.05, 0.025, 0.01, 0.0075, 0.005, 0.0025, 0.001, 0.0001, or 0.00001 parts (or none/no detectable), individually or in any combination, of thiol, amine, carboxylate, and/or hydroxyl functionalization per 100 $MnO_2$ units, relative to a total metal oxide weight.

The nanocomposite may include no more than 1, 0.75, 0.5, 0.25, 0.1, 0.01, 0.001, 0.0001, or 0.00001 wt. %, individually or in any combination, of titanium dioxide ($TiO_2$), titanium aluminum nitride ($Ti_2AlN$), iron (III) oxide ($Fe_3O_4$), aluminum nitride (AlN), zinc oxide (ZnO), and/or silicon dioxide ($SiO_2$), relative to a total metal oxide weight.

The nanocomposite may include no more than 1, 0.75, 0.5, 0.25, 0.1, 0.01, 0.001, 0.0001, or 0.00001 atom of cerium (Ce), relative to 100 atoms of manganese (Mn).

The carbon materials in the nanocomposite may include no more than 1, 0.75, 0.5, 0.25, 0.1, 0.01, 0.001, 0.0001, or 0.00001 wt. %, preferably less than 0.9 wt. %, preferably less than 0.8 wt. %, preferably less than 0.7 wt. %, preferably less than 0.6 wt. %, preferably less than 0.5 wt. %, preferably less than 0.4 wt. %, preferably less than 0.3 wt. %, preferably less than 0.2 wt. %, preferably less than 0.1 wt. %, individually or together, carbon nanotubes (CNTs) and/or carbon dots, relative to total nanocomposite weight.

The nanocomposite no more than 1, 0.75, 0.5, 0.25, 0.1, 0.01, 0.001, 0.0001, or 0.00001 wt. %, preferably less than 0.9 wt. %, preferably less than 0.8 wt. %, preferably less than 0.7 wt. %, preferably less than 0.6 wt. %, preferably less than 0.5 wt. %, preferably less than 0.4 wt. %, preferably less than 0.3 wt. %, preferably less than 0.2 wt. %, preferably less than 0.1 wt. %, silver bromide (AgBr), relative to a total metal oxide weight.

The nanocomposite no more than 1, 0.75, 0.5, 0.25, 0.1, 0.01, 0.001, 0.0001, or 0.00001 wt. %, preferably less than 0.9 wt. %, preferably less than 0.8 wt. %, preferably less than 0.7 wt. %, preferably less than 0.6 wt. %, preferably less than 0.5 wt. %, preferably less than 0.4 wt. %, preferably less than 0.3 wt. %, preferably less than 0.2 wt. %, preferably less than 0.1 wt. % tungsten oxide (WO3), relative to a total nanocomposite weight.

The nanocomposite no more than 1, 0.75, 0.5, 0.25, 0.1, 0.01, 0.001, 0.0001, or 0.00001 wt. %, preferably less than 0.9 wt. %, preferably less than 0.8 wt. %, preferably less than 0.7 wt. %, preferably less than 0.6 wt. %, preferably less than 0.5 wt. %, preferably less than 0.4 wt. %, preferably less than 0.3 wt. %, preferably less than 0.2 wt. %, preferably less than 0.1 wt. % copper sulfide (CuS), relative to total nanocomposite weight.

The nanocomposite no more than 1, 0.75, 0.5, 0.25, 0.1, 0.01, 0.001, 0.0001, or 0.00001 wt. %, preferably less than 0.9 wt. %, preferably less than 0.8 wt. %, preferably less than 0.7 wt. %, preferably less than 0.6 wt. %, preferably less than 0.5 wt. %, preferably less than 0.4 wt. %, preferably less than 0.3 wt. %, preferably less than 0.2 wt. %, preferably less than 0.1 wt. %, individually or in any combination, copper oxide (CuO), aluminosilicate, and/or WO3, relative to total nanocomposite weight.

The nanocomposite no more than 1, 0.75, 0.5, 0.25, 0.1, 0.01, 0.001, 0.0001, or 0.00001 wt. %, preferably less than 0.9 wt. %, preferably less than 0.8 wt. %, preferably less than 0.7 wt. %, preferably less than 0.6 wt. %, preferably less than 0.5 wt. %, preferably less than 0.4 wt. %, preferably less than 0.3 wt. %, preferably less than 0.2 wt. %, preferably less than 0.1 wt. %, individually or in combination, elemental state Co and/or Fe, relative to total nanocomposite weight.

The nanocomposite no more than 0.1, 0.075, 0.05, 0.025, 0.01, 0.01, 0.001, 0.0001, or 0.00001 wt. % of any noble metal, relative to total nanocomposite weight.

The nanocomposite may include no more than 10, 7.5, 5, 4, 3, 2, 1, 0.5, 0.1, 0.01, 0.001, 0.0001, or 0.00001 wt. %, preferably less than 9 wt. %, preferably less than 8 wt. %, preferably less than 7 wt. %, preferably less than 6 wt. %, preferably less than 5 wt. %, preferably less than 4 wt. %, preferably less than 3 wt. %, preferably less than 2 wt. %, preferably less than 1 wt. %, preferably less than 0.9 wt. %, preferably less than 0.8 wt. %, preferably less than 0.7 wt. %, preferably less than 0.6 wt. %, preferably less than 0.5 wt. %, preferably less than 0.4 wt. %, preferably less than 0.3 wt. %, preferably less than 0.2 wt. %, preferably less than 0.1 wt. % magnesium oxide (MgO), relative to a total metal oxide weight. The nanocomposite may include no clay, e.g., no more than 5, 4, 3, 2.5, 2, 1, 0.5, 0.1, 0.01, 0.001, 0.0001, or 0.00001 wt. %, relative to total nanocomposite weight, of clay.

The nanocomposite obtained may include no more than 1, 0.75, 0.5, 0.25, 0.1, 0.01, 0.001, 0.0001, or 0.00001 wt. % of carbonaceous material besides the graphitic carbon nitride, preferably less than 0.9 wt. %, preferably less than 0.8 wt. %, preferably less than 0.7 wt. %, preferably less than 0.6 wt. %, preferably less than 0.5 wt. %, preferably less than 0.4 wt. %, preferably less than 0.3 wt. %, preferably less than 0.2 wt. %, preferably less than 0.1 wt. %, preferably less than 0.05 wt. %, and preferably less than 0.01 wt. % of carbonaceous material besides the graphitic carbon nitride. The g-$C_3N_4$ may not be nitrogen deficient. The g-$C_3N_4$ in the nanocomposite may include no more than inevitable traces of boron, e.g., no more than 5, 4, 3, 2.5, 2, 1, 0.5, 0.1, 0.01, 0.001, 0.0001, or 0.00001 wt. %, relative to total nanocomposite weight, of boron. The carbon materials in the nanocomposite include no more than 0.01 wt. % nanotubes and/or nanorods, relative to total nanocomposite weight.

The morphology of the g-$C_3N_4$ may be nanowires, nanospheres, nanocrystals, nanorectangles, nanotriangles, nanopentagons, nanohexagons, nanoprisms, nanodisks, nanocubes, nanoribbons, nanoblocks, nanotoroids, nanodiscs, nanobarrels, nanogranules, nanowhiskers, nanoflakes, nanofoils, nanopowders, nanoboxes, nanobeads, nanobelts, nanourchins, nanoflowers, nanostars, tetrapods, etc., and mixtures thereof. The g-$C_3N_4$ in the nanocomposite may have a sheet morphology, e.g., at least 75, 80, 85, 90, 92.5, 95, 97.5, 98, 99, 99.1, 99.5, or 99.9 wt. % of the carbonaceous material having sheet morphology.

The nanocomposite may include no more than 10, 7.5, 5, 4, 3, 2, 1, 0.5, 0.1, 0.01, 0.001, 0.0001, or 0.00001 wt. %, preferably 9 wt. %, preferably 8 wt. %, preferably 7 wt. %, preferably 6 wt. %, preferably 5 wt. %, preferably 4 wt. %, preferably 3 wt. %, preferably 2 wt. %, preferably 1 wt. %, preferably 0.5 wt. % $Mn_3O_4$, relative to total manganese oxide weight.

The nanocomposite may include no more than 1, 0.75, 0.5, 0.25, 0.1, 0.01, 0.001, 0.0001, or 0.00001 wt. %, preferably less than 0.9 wt. %, preferably less than 0.8 wt. %, preferably less than 0.7 wt. %, preferably less than 0.6 wt. %, preferably less than 0.5 wt. %, preferably less than 0.4 wt. %, preferably less than 0.3 wt. %, preferably less than 0.2 wt. %, preferably less than 0.1 wt. %, V-doped ZnO, relative to total nanocomposite weight.

The nanocomposite may include no more than 1, 0.75, 0.5, 0.25, 0.1, 0.01, 0.001, 0.0001, or 0.00001 wt. %, %, preferably less than 0.9 wt. %, preferably less than 0.8 wt. %, preferably less than 0.7 wt. %, preferably less than 0.6 wt. %, preferably less than 0.5 wt. %, preferably less than 0.4 wt. %, preferably less than 0.3 wt. %, preferably less than 0.2 wt. %, preferably less than 0.1 wt. %, individually or in any combination, of $K_2Ti_8O_{17}$, $Al_2O_3$, ZnO, $Fe_3O_4$, $CeFeO_3$, $GdFeO_3$, $LaFeO_3$, $BaTiO_3$, $CaTiO_3$, $SrTiO_3$, $CaZrO_3$, $PbTiO_3$, $Mg_{1-x}Ni_xFe_2O_4$ (x=0.0, 0.6, 1.0), Ag, $CoFe_2O_4$, $CuFe_2O_4$, $MnFe_2O_4$, $NiFe_2O_4$, $ZnFe_2O_4$, $Cu_{1-x}Cd_xFe_2O_4$, $Zn_{0.7}Ni_{0.15}Cu_{0.15}Fe_2O_4$, $Zn_{0.3}Ni_{0.7-x}Co_xFe_2O_4$ ($0 \leq x \leq 0.7$), $Mn_{0.1}Mg_{0.2}$ (Co, Ni, Zn)$_{0.7}Fe_2O_4$, $LaCo_{0.5}Fe_{0.5}O_3$, $Mg_{0.1}$—$Co_{0.9}Fe_2O_4$, $La_{1-x}Gd_xCr_{1-y}Ni_yO_3$, $Gd_2FeCrO_6$, $KTaO_3$, $NaTaO_3$, $NaNbO_3$, $KNbO_3$, $Mg_{1-x}Ni_xFe_2O_4$, $Cu_{0.5}Cd_{0.25}Co_{0.25}Fe_{2-x}O_4$, $Zn_{0.5}Co_{0.5}La_xFe_{2-x}O_4$, $Pr_2Ti_2O_7$, $SiO_2$, $TiO_2$, ZnS, $Bi_4O_5I_2$, $SrFe_{0.5}Ta_{0.5}O_3$, $La_{0.8}Ba_{0.2}TiO_{3.5-\delta}$, $LaTiO_{3.5-\delta}$, $NaNbO_3$, and/or $LaFeO_3$, relative to a total metal oxide weight The nanocomposite may include no more than 10, 7.5, 5, 4, 3, 2, 1, 0.5, 0.1, 0.01, 0.001, 0.0001, or 0.00001 wt. %, preferably less than 9 wt. %, preferably less than 8 wt. %, preferably less than 7 wt. %, preferably less than 6 wt. %, preferably less than 5 wt. %, preferably less than 4 wt. %, preferably less than 3 wt. %, preferably less than 2 wt. %, preferably less than 1 wt. %, preferably less than 0.9 wt. %, preferably less than 0.8 wt. %, preferably less than 0.7 wt. %, preferably less than 0.6 wt. %, preferably less than 0.5 wt. %, preferably less than 0.4 wt. %, preferably less than 0.3 wt. %, preferably less than 0.2 wt. %, preferably less than 0.1 wt. %, individually or in any combination, relative to total metal content, of any of zinc (Zn), cerium (Ce), gadolinium (Gd), lanthanum (La), barium (Ba), titanium (Ti), calcium (Ca), strontium (Sr), zirconium (Zr), lead (Pb), nickel (Ni), silver (Ag), gold (Au), cobalt (Co), copper (Cu), manganese (Mn), cadmium (Cd), tungsten (W), tantalum (Ta), niobium (Nb), praseodymium (Pr), and/or bismuth (Bi).

The nanocomposite includes no more than 1, 0.75, 0.5, 0.25, 0.1, 0.01, 0.001, 0.0001, or 0.00001 wt. %, preferably less than 0.9 wt. %, preferably less than 0.8 wt. %, preferably less than 0.7 wt. %, preferably less than 0.6 wt. %, preferably less than 0.5 wt. %, preferably less than 0.4 wt. %, preferably less than 0.3 wt. %, preferably less than 0.2 wt. %, preferably less than 0.1 wt. %, individually or in any combination, relative to total carrier weight, of $SiO_2$, $TiO_2$, ZnO, and/or ZnS.

The purpose of the g-$C_3N_4$@$MnO_2$/$MgAl_2O_4$ nanocomposite described may be to provide a highly specific and controlled formulation of the composite for anticancer applications, where the presence of various materials may be carefully limited to ensure the desired properties. Specifically, the nanocomposite may include no more than 0.1, 0.01, 0.001, 0.0001, or 0.00001 parts of thiol, amine, carboxylate, and hydroxyl functional groups per 100 $MnO_2$ units (or per $MnO_2$ unit), and may restrict the content of various other materials (e.g., $TiO_2$, ZnO, $Fe_3O_4$, CNTs, noble metals, etc.) to ensure a defined composition. The nanocomposite may also limit specific metal oxide and carbon material content, as well as certain doping and alloying elements, to maintain the efficacy and safety of the material. These restrictions aim to enhance the nanocomposite's performance as an anticancer agent while minimizing undesired side effects or interactions with biological systems.

The nanocomposite may be porous. A porous material is the one that forms a porous bulk solid. Pores may be micropores, mesopores, macropores, and/or a combination thereof. The pores exist in the bulk material, not necessarily in the molecular structure of the material. The term 'microporous' means that nanocomposite have pores with an average pore width (i.e., diameter) of less than 2 nm, e.g., in a range with an upper limit of 2, 1, 0.9, 0.75, 0.5, 0.25, 0.1, 0.05, or 0.01 nm, and/or a lower limit of 0.00001, 0.0001, 0.001, 0.01, 0.1, 0.25, 0.5, 0.75, or 1 nm. The term 'mesoporous' means the pores of the nanocomposite have an average pore width of 2 to 50 nm, though this may include subranges within this general range, e.g., a minimum diameter of 2, 3, 5, 10, 15, 20, 25, or 35 nm, and/or a maximum diameter of 50, 45, 40, 35, 30, 25, 20, 15, or 10 nm. The term 'macroporous' means the pores of nanocomposite have an average pore width larger than 50 nm, e.g., at least 55, 75, 100, 250, 500, 750, or 1000 nm. Pore size may be determined by methods including, but not limited to, gas adsorption (e.g., $N_2$ adsorption), mercury intrusion porosimetry, and imaging techniques such as scanning electron microscopy (SEM), and X-ray computed tomography (XRCT).

A Brunauer-Emmett-Teller (BET) specific surface area of the nanocomposite may be in a range of from 16.2 to 20.2 square meters per gram ($m^2/g$), preferably 16.4 to 20.0 $m^2/g$, preferably 16.6 to 19.8 $m^2/g$, preferably 16.8 to 19.6 $m^2/g$, preferably 17.0 to 19.4 $m^2/g$, preferably 17.2 to 19.2 $m^2/g$, preferably 17.4 to 19.0 $m^2/g$, preferably 17.6 to 18.8 $m^2/g$, preferably 17.8 to 18.6 $m^2/g$, and preferably 18.0 to 18.4 $m^2/g$. The surface area of the nanocomposite may be 18.7±3.33, 2.5, 2, 1.5, 1, 0.75, 0.67, 0.5, 0.33, 0.25, 0.125, 0.1, 0.05, or 0.01 $m^2/g$. The BET hypothesis is the foundation for a significant analysis method for determining the specific surface area of a material. It attempts to explain the physical adsorption of gas molecules on a solid surface. Specific surface area is a property of solids, which is the total surface area of a material per unit of mass, solid or bulk volume, or cross-sectional area. The pore diameter, pore volume, and BET surface area may be measured by gas adsorption analysis, preferably $N_2$ adsorption analysis (e.g., $N_2$ adsorption isotherms).

An average pore diameter of the nanocomposite, according to Barrett-Joyner-Halenda (BJH) measurement method, may be in a range of from 5 to 15 nm, preferably 6 to 14 nm, preferably 7 to 13 nm, preferably 8 to 12 nm, and preferably 9 to 11 nm. The nanocomposite may have an average pore diameter of 8.34±2, 1.5, 1, 0.75, 0.67, 0.5, 0.33, 0.25, 0.125, 0.1, 0.05, or 0.01 nm. An average pore volume of the nanocomposite, according to the BJH measurement method, may be in a range of from 0.025 to 0.075 $cm^3/g$, preferably 0.030 to 0.070 $cm^3/g$, preferably 0.035 to 0.065 $cm^3/g$, preferably 0.040 to 0.060 $cm^3/g$, and preferably 0.045 to 0.055 $cm^3/g$. The average pore volume of the nanocomposite, according to the BJH measurement method, may be 0.050±0.025, 0.01, 0.001, 0.0001, or 0.00001 cm$^3$/g.

The average pore distribution of the nanocomposite may include, but is not limited to, crystalline average pore distribution, bimodal, trimodal, multimodal, narrow, broad, and Gaussian. The average pore distribution of the nanocomposite may be unimodal. indicating a single dominant pore size within the material. This unimodal distribution suggests that the nanocomposites possess a relatively narrow pore size range, resulting in more uniform pore structures and enhancing specific properties such as adsorption capacity, catalytic activity, or surface reactivity.

The nanocomposite may have a (220) spinel interplanar spacing in a range of from 0.258 to 0.338 nm, preferably 0.263 to 0.333 nm, preferably 0.268 to 0.328 nm, preferably 0.273 to 0.323 nm, preferably 0.278 to 0.318 nm, preferably 0.283 to 0.313 nm, preferably 0.288 to 0.308 nm, and preferably 0.293 to 0.303 nm, according to selected area diffraction (SAED). The nanocomposite may have a (400) spinel interplanar spacing in a range of from 0.165 to 0.245 nm, preferably 0.170 to 0.240 nm, preferably 0.175 to 0.235 nm, preferably 0.180 to 0.230 nm, preferably 0.185 to 0.225 nm, preferably 0.190 to 0.220 nm, preferably 0.195 to 0.215 nm, and preferably 0.200 to 0.210 nm, according to SAED. The nanocomposite may include a (002) $MnO_2$ interplanar spacing in a range of from 0.106 to 0.186 nm, preferably 0.116 to 0.176 nm, preferably 0.126 to 0.166 nm, preferably 0.136 to 0.156 nm preferably, according to SAED. The nanocomposite may include a (211) $Al_2O_3$ interplanar spacing in a range of from 0.093 to 0.173 nm, 0.093 to 0.173 nm, preferably 0.103 to 0.163 nm, preferably 0.113 to 0.153 nm, preferably 0.123 to 0.143 nm, according to SAED.

The nanocomposite may have a (220) spinel interplanar spacing may be 0.298±2% nm, (400) spinel interplanar spacing may be 0.205±2% nm, (002) $MnO_2$ interplanar spacing may be 0.146±2% nm, and (211) $Al_2O_3$ interplanar spacing may be 0.133±2% nm, according to SAED.

An XRD spectrum of the nanocomposite under Cu-filtered Cu Kα radiation (1.5418 Å) powered at 45 kilovolt (kV) and 10 milliamperes (mA) may have 20 peaks of a $MnO_2$ pyrolusite phase at 28.4±1, 40.5±1, 44.9±1, 56.0±1, 66.4±1, and/or 79.1±1°, a $MgAl_2O_4$ spinel phase at 19.1±1, 31.3±1, 44.8±1, 56.1±1, 59.5±1, 74.09±1, and/or 78.1±1°, an MgO cubic phase at 42.8±1, 62.2±1, and/or 74.6±1°, an $Al_2O_3$ phase at 31.3±1, 34.3±1, and/or 61.6±1°, and/or g-$C_3N_4$-related diffractions at 18.8±1, 28.2±1, 35.5±1, 40.7±1, 44.6±1, and/or 73.7±1°.

No more than 5%, preferably no more than 4 wt. %, preferably no more than 3 wt. %, preferably no more than 2 wt. %, preferably no more than 1 wt. %, preferably no more than 0.5 wt. %, preferably no more than 0.4 wt. %, preferably no more than 0.3 wt. %, preferably no more than 0.2 wt. %, preferably no more than 0.1 wt. %, preferably no more than 0.05 wt. %, and preferably no more than 0.01 wt. % relative intensity of any other phase may be detected in the XRD spectrum.

The MgO may have a cubic crystal structure. Alternatively or additionally, MgO may exist in other crystal phases, including hexagonal, monoclinic, tetragonal, rhombohedral, and orthorhombic phases.

$MgAl_2O_4$ may have a spinel phase. The spinel phase is a mixed oxide with the general formula $AB_2O_4$, including one divalent cation ($A^{2+}$) and two trivalent cations ($B^{3+}$). The unit cell consists of a face-centered cubic arrangement of oxygen ions, containing 32 $O^{2-}$ ions, with 64 tetrahedral and 32 octahedral sites occupied by $A^{2+}$ and $B^{3+}$ cations. When one-half of the octahedral interstices are occupied by $B^{3+}$ cations and one-eighth of the tetrahedral sites are occupied by $A^{2+}$ cations, the spinel phase is termed 'normal.' Conversely, when tetrahedral sites are occupied by half of the $B^{3+}$ and octahedral sites by the other half along with A2+, the spinel phase is termed 'inverse'.

$MgAl_2O_4$ can be used in various applications, such as in metallurgical, electrochemical, radio-technical, and chemical industrial fields owing to its high thermal stability (melting point at 2135 degrees Celsius (° C.), high hardness (16 gigapascal (GPa)), high mechanical resistance, high resistance against chemical attack, wide band gap energy, high electrical resistivity, relatively low thermal expansion coefficient (9.10$^{-6}$ 1/° C.) between 3° and 1400° C., low dielectric constant, low density (3.58 gram per cubic centimeter (g/cm$^3$)), high thermal shock resistance, hydrophobicity, and low surface acidity.

The method of inhibiting the cancer cell viability may include contacting cancer cells and the nanocomposite. The mass relationship of the nanocomposite may be in a range of from 9 to 11:4 to 6:84 to 86, preferably 9.5 to 10.5:4.5 to 5.5:84.5 to 85.5, and more preferably 10:5:85. The nanocomposite of the present disclosure may then be administered orally, systemically, parenterally, by inhalation spray, rectally, or topically in dosage unit formulations containing conventional non-toxic pharmaceutically acceptable carriers, adjuvants, and vehicles as desired.

The nanocomposite being at a concentration in a range of from 10.0 to 500 microgram per milliliter (μg/mL), preferably 35.0 to 475 μg/mL, preferably 60.0 to 450 μg/mL, preferably 85.0 to 425 μg/mL, preferably 110.0 to 400 μg/mL, preferably 135.0 to 375 μg/mL, preferably 160.0 to 350 μg/mL, preferably 185.0 to 325 μg/mL, preferably 210.0 to 300 μg/mL, preferably 235.0 to 275 μg/mL, during contacting the cancer cells, thereby inhibiting the growth of the cancer cells by at least 85%, preferably 90%, preferably 95%, preferably 100%, preferably 105%, preferably 110%, preferably 115%, and preferably 120%. The $IC_{50}$ may be 119.78 μg/mL, and the maximum dose (500 μg/mL) may show an 88.1% inhibition of the MCF-7 cancer cells. The $IC_{50}$ may be 96.5 μg/mL, and the maximum dose (500 μg/mL) may show a 91.3% inhibition of the HepG-2 cancer cells. The nanocomposite acts as an antiproliferation agent against the HepG-2 human hepatocellular carcinoma cells and the MCF-7 human breast carcinoma cancer cells.

The method of administration of the steroid or an analog or derivative thereof may be oral. The nanocomposite may be administered by injection, such as, for example, through a peritumoral injection. Topical administration can also involve the use of transdermal administration, such as transdermal patches or iontophoresis devices. The term parenteral, as used herein, may include intravesical, intradermal, transdermal, subcutaneous, intramuscular, intralesional, intracranial, intrapulmonary, intracardial, intrasternal, and sublingual injections, or infusion techniques.

Injectable preparations, for example, sterile injectable aqueous or oleaginous suspensions, can be Formulated according to the known art using suitable dispersing or wetting agents and suspending agents. The sterile injectable preparation can also be a sterile injectable solution or suspension in a nontoxic, parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, any fixed oil can be employed, including synthetic mono- or diglycerides. In addition, fatty acids such as oleic acid find use in the preparation of injectables. Dimethyl acetamide, surfactants including ionic and non-ionic detergents, and polyethylene glycols can be used. Mixtures of solvents and wetting agents, such as those discussed above, are also useful. Suppositories for rectal administration of the compound or an analogue or derivative thereof can be prepared by mixing the steroid or an analogue or derivative thereof with a suitable non-irritating excipient such as cocoa butter, synthetic mono- di- or triglycerides, fatty acids, and polyethylene glycols that are solid at ordinary temperatures but liquid at the rectal temperature and will therefore melt in the rectum and release the drug.

Solid dosage forms for oral administration can include capsules, tablets, pills, powders, and granules. In such solid dosage forms, the compounds of this disclosure are ordinarily combined with one or more adjuvants appropriate to the indicated route of administration. If administered a contemplated steroid or an analogue or derivative thereof can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in a dispersion of the active compound in hydroxypropyl methylcellulose. In the case of capsules, tablets, and pills, the dosage forms can also include buffering agents such as sodium citrate, magnesium or calcium carbonate, or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated steroid or an analog or derivative thereof of the present disclosure can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also include adjuvants, such as wetting agents, emulsifying and suspending, agents, and sweetening, flavoring, and perfuming agents.

The cancer cells are MCF-7 human breast carcinoma cancer cells, and the concentration of the nanocomposite may be in a range of from 100 to 450 µg/mL, 100 to 450 µg/mL, preferably 110 to 440 µg/mL, preferably 120 to 430 µg/mL, preferably 130 to 420 µg/mL, preferably 140 to 410 µg/mL, preferably 150 to 400 µg/mL, preferably 160 to 390 µg/mL, preferably 170 to 380 µg/mL, preferably 180 to 370 µg/mL, preferably 190 to 360 µg/mL, preferably 200 to 350 µg/mL, preferably 210 to 340 µg/mL, preferably 220 to 330 µg/mL, preferably 230 to 320 µg/mL, preferably 240 to 310 µg/mL, preferably 250 to 300 µg/mL, preferably 260 to 290 µg/mL, preferably 270 to 280 µg/mL, and preferably $IC_{50}$ against the MCF-7 human breast carcinoma cancer cells may be 119.78±20, 15, 10, 7.5, 5, 4, 3.33, 2.5, 2, 1.5, 1, 0.75, 0.67, 0.5, 0.33, 0.25, 0.125, 0.1, 0.05, or 0.01 µg/mL. The cancer cells are HepG-2 human hepatocellular carcinoma cells, and the concentration of the nanocomposite in the contacting may be in a range of from 75 to 350 µg/mL, preferably 85 to 340 µg/mL, preferably 95 to 330 µg/mL, preferably 105 to 320 µg/mL, preferably 115 to 310 µg/mL, preferably 125 to 300 µg/mL, preferably 135 to 290 µg/mL, preferably 145 to 280 µg/mL, preferably 155 to 270 µg/mL, preferably 165 to 260 µg/mL, preferably 175 to 250 µg/mL, preferably 185 to 240 µg/mL, preferably 195 to 230 µg/mL, preferably 205 to 220 µg/mL, and preferably 215 to 210 µg/mL, preferably $IC_{50}$ against the HepG-2 human hepatocellular carcinoma cells may be 96.56±15, 10, 7.5, 5, 4, 3.33, 2.5, 2, 1.5, 1, 0.75, 0.67, 0.5, 0.33, 0.25, 0.125, 0.1, 0.05, or 0.01 µg/mL.

The methods for inhibiting cancer and other proliferative disorders described herein inhibit, remove, eradicate, reduce, regress, diminish, arrest, or stabilize a cancerous tumor, including at least one of the tumor growth, tumor cell viability, tumor cell division, and proliferation, tumor metabolism, blood flow to the tumor and metastasis of the tumor. After contacting cancer cells, the size of a tumor, whether by volume, weight, or diameter, may be reduced by at least 5%, 10%, 15%, 20%, 25%, 30%, 40%, 50%, 60%, 70%, 75%, relative to the tumor size before treatment. After contacting cancer cells, the size of a tumor may not reduce but may be maintained the same as the tumor size before treatment. Methods of assessing tumor size include, but are not limited to, computed tomography scan (CT scan), magnetic resonance imaging (MRI), dynamic contrast-enhanced magnetic resonance imaging (DCE-MRI), and positron emission tomography scan (PET scan).

The dosage and inhibition duration are dependent on factors such as the bioavailability of a drug, administration mode, toxicity of a drug, gender, age, lifestyle, body weight, the use of other drugs and dietary supplements, cancer stage, tolerance, and resistance of the body to the administered drug, etc., then determined and adjusted accordingly. The nanocomposite may be administered in a single dose or multiple individual divided doses. The interval of time between the administration of the nanocomposite and the administration of one or more additional therapies may be about 1 to 5 minutes (min), 1 to 30 min, 30 min to 60 min, 1 hour (h), 1 to 2 h, 2 to 6 h, 2 to 12 h, 12 to 24 h, 1 to 2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11 to 15 weeks. 15 to 20 weeks, 20 to 30 weeks, 30 to 40 weeks, 40 to 50 weeks, 1 month, 2 months, 3 months, 4 months 5 months, 6 months, 7 months, 8 months, 9 months, 10 months, 11 months, 12 months, 1 year, 2 years, or any period in between. The nanocomposite and one or more additional therapies are administered less than 1 day, 1 day, 2 days, 3 days, 4 days, 1 week, 2 weeks, 3 weeks, 4 weeks, one month, 2 months, 3 months, 6 months, 1 year, 2 years, or 5 years apart.

The nanocomposite of the present disclosure or a pharmaceutical composition thereof may be used in combination with one or more other antineoplastic or chemotherapeutic agents. A non-limiting list of examples of chemotherapeutic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosamide, irinotecan, lomustine, mechclorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cis-platin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguaniue), tipifarnib. Examples of antineoplastic agents which are protein kinase inhibitors include imatinib, erlotinib, sorafenib, sunitinib, dasatinib, nilotinib, lapatinib, gefitinib, temsirolimus, everolimus, rapamycin, bosutinib, pazopanib, axitinib, neratinib, vatalanib, pazopanib, midostaurin, and enzastaurin. Examples for antineoplastic agents which are antibodies include trastuzumab, cetuximab, panitumumab, rituximab, bevacizumab, mapatumumab, conatumumab, lexatumumab and the like.

EXAMPLES

The following examples demonstrate a method inhibiting cancer cell viability via a nanocomposite. The examples are provided solely for illustration and are not to be construed as limitations of the present disclosure, as many variations thereof are possible without departing from the spirit and scope of the present disclosure.

Example 1: Fabrication of g-$C_3N_4$@$MnO_2$/$MgAl_2O_4$ (10:5:8 5, Wt. %) Nanocomposite According to the present disclosure, magnesium nitrate, and aluminum nitrate were added together in one beaker with manganese chloride, in predetermined amount (here, stoichiometric), to produce a 10% $MnO_2$/$MgAl_2O_4$. Further, about 10 g of menthol as fuel was added to the beaker, followed by 30 mL of distilled water. The beaker was heated till a clear solution was obtained, heated further till dryness. The product was ground in a mortar, transferred to a 150 mL porcelain dish, and calcined at 700° C. for 3.0 hours. Furthermore, the 10% $MnO_2$/$MgAl_2O_4$ product was cooled down to room temperature and weighed, ground with urea in an amount suitable (here, 2 g urea to 20 g of the 10% $MnO_2$/$MgAl_2O_4$ product, but depending upon the reaction conditions, this may be 5, 10, 15, 20, 25, 33, 50, 100, 150, 250, 500, or 1000 parts by weight of urea to 100 parts by weight of 10% $MnO_2$/$MgAl_2O_4$, and optionally no more than 100,000, 50,000, 25,000, 10,000, 5,000, 1,000, 750, 500, 400, 333, 250, 125, 100, 75, 50, 25, 20, 15, or 10 parts by weight urea to 100 parts) to produce g-$C_3N_4$@$MnO_2$/$MgAl_2O_4$ (10:5:85, wt. %) nanohybrid/nanocomposite. The quadruple mixture was returned, and heated to 600° C. for 1.0 h in a covered porcelain crucible, and subsequently, the g-$C_3N_4$@$MnO_2$/$MgAl_2O_4$ (10:5:85, wt. %) nanohybrid was collected.

Example 2: Characterization

According to the present disclosure, X-ray diffraction (XRD) was used to identify the crystalline states in each specimen studied, employing the JDX-8030 X-ray (JEOL), made in Japan. Cu-filtered Cu-Kα radiation (1.5418 Å) powered at 45 kV and 10 mA was used to run the patterns. The specimens were tested at ambient temperatures in a range of 2θ=5° to 80°. The surface morphologies of the obtained samples were analyzed by transmission electron microscopy (TEM), selected area electron diffraction (SAED), and high-resolution transmission electron microscopy (HRTEM) images, obtained using a Tecnai-G20 (USA) transmission electron microscope with a 200 kV speed voltage.

Results and Discussion

As mentioned above, XRD was used to examine the crystallinity and phase identification of the g-$C_3N_4$@$MnO_2$/$MgAl_2O_4$ catalyst, the results are depicted in FIG. 1. As can be seen from FIG. 1, high crystalline nature of the powders is indicated by the strong peaks. The diffraction patterns are compared to the standard COD cards to demonstrate the presence of $MnO_2$, MgO, $MgAl_2O_4$, $Al_2O_3$, and g-$C_3N_4$ phases. The diffractions of $MgAl_2O_4$ spinel were recorded at 2θ values of 44.8°, 56.1°, 59.5°, 74.09°, 78.1°, 19.1°, and 31.3°. The standard COD card number 9001364 states that the diffractions originated from the (111), (220), (400), (422), (511) (620), and (622) planes, respectively. MgO (COD card, No. 9000499) showed a cubic phase at 2θ values of 42.8°, 62.2°, and 74.6°. The (200), (220), and (311), respectively, are represented by these lines. It was previously reported that MgO was present together with the $MgAl_2O_4$ spinel phase. The pyrolusite phase of $MnO_2$ (COD No. 2105790) is closely matched with the diffraction lines observed at 28.4°, 40.5°, 44.9°, 56.0°, 66.4°, and 79.1°. According to COD No. 1534042, the g-$C_3N_4$ diffractions were detected at 18.8°, 28.2°, 35.5°, 40.7°, 44.6°, and 73.7°. At 31.3°, 34.3°, and 61.6°, $Al_2O_3$ traces were detected (COD No. 4002418). There were no further phases found, suggesting that g-$C_3N_4$@$MnO_2$/$MgAl_2O_4$ was successfully fabricated.

Figure 2A:
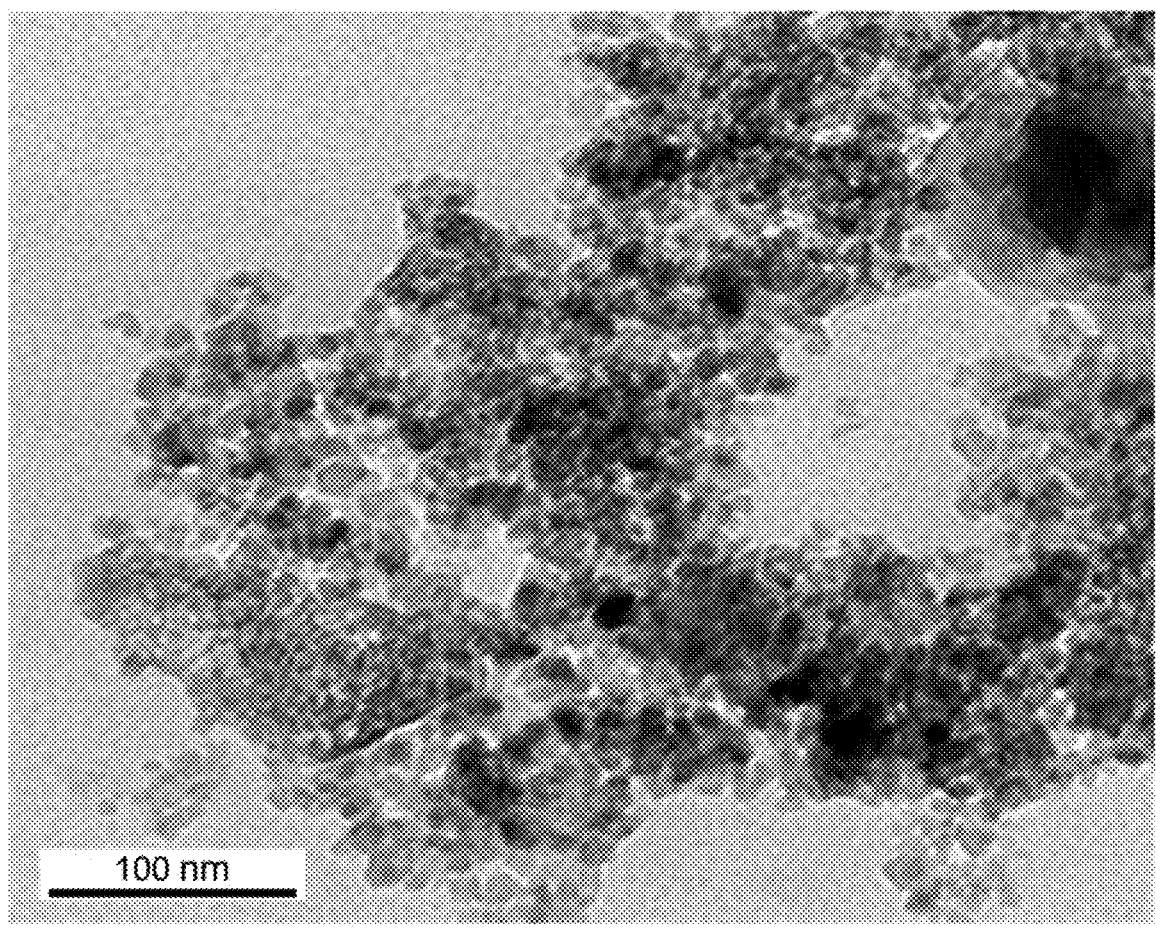
FIG. 2A is a transmission electron microscopy (TEM) image of an inventive g-$C_3N_4$@$MnO_2$/$MgAl_2O_4$ nanocomposite.
Figure 2B:
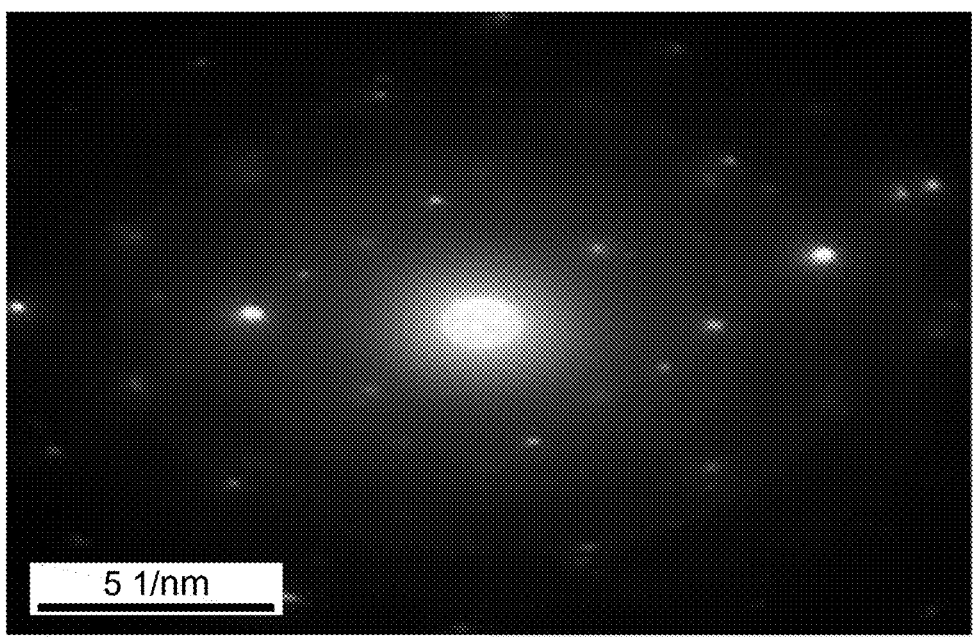
FIG. 2B depicts the selected area electron diffraction (SAED) analysis result for an inventive g-$C_3N_4$@$MnO_2$/$MgAl_2O_4$ nanocomposite.
Figure 2C:
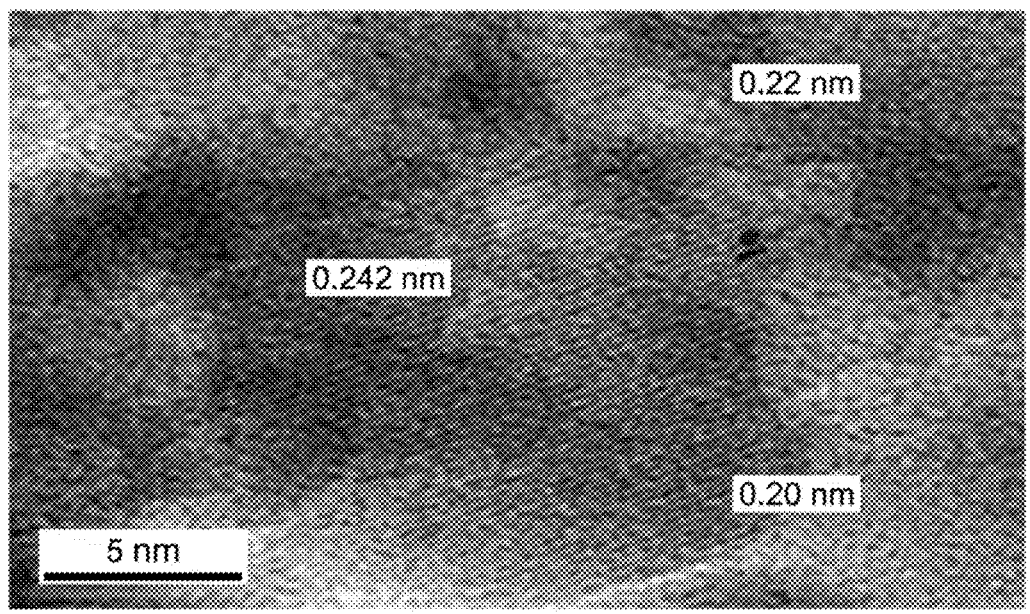
FIG. 2C is a high-resolution transmission electron microscopy (HRTEM) image of an inventive g-$C_3N_4$@$MnO_2$/$MgAl_2O_4$ nanocomposite.
Figure 2D:
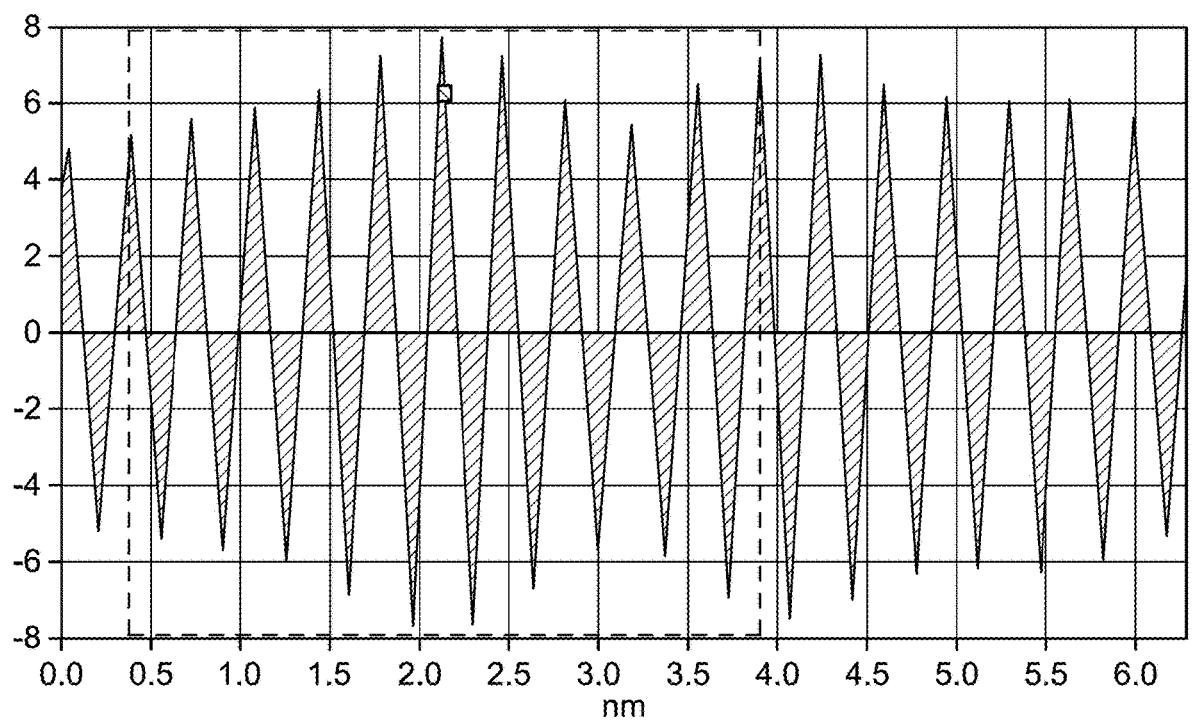
FIG. 2D is a fast Fourier transform (FFT) spectra of an inventive g-$C_3N_4$@$MnO_2$/$MgAl_2O_4$ nanocomposite.
Figure 2E:
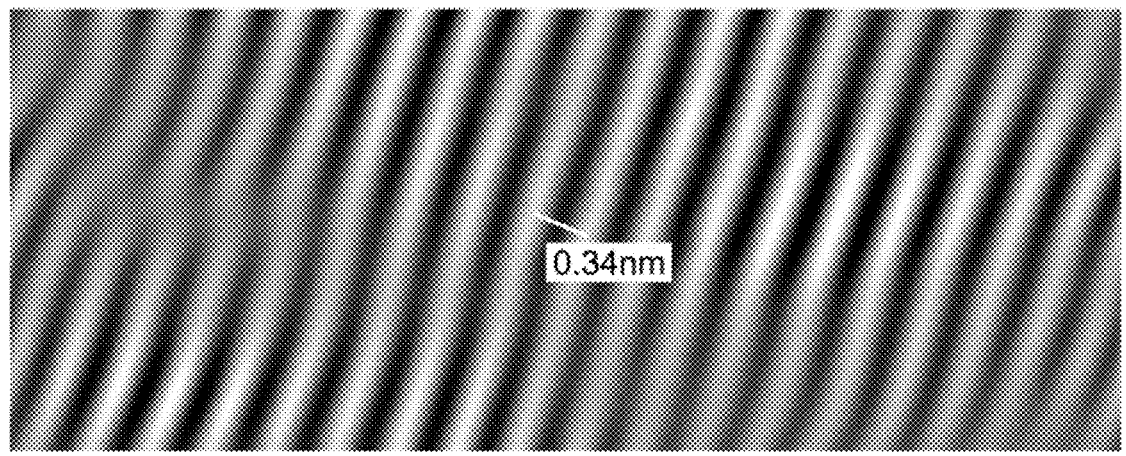
FIG. 2E is an inverse fast Fourier transform (IFFT) spectra of an inventive g-$C_3N_4$@$MnO_2$/$MgAl_2O_4$ nanocomposite.

Further, TEM images of g-$C_3N_4$@$MnO_2$/$MgAl_2O_4$ nanocomposite are shown in FIG. 2A. The TEM image shows the dispersion of homogeneous spherical metal oxides nanoparticles with size 7.9 nm on two-dimensional porous structure constructed with curled and wrinkled nanosheets and platelets of the g-$C_3N_4$. The corresponding SAED pattern of the nanocomposite, as shown in FIG. 2B, reveals diffraction spots with interplanar spacing of 0.298 nm, 0.205 nm, 0.146 nm, and 0.133 nm due to (220, spinel), (400, spinel), (002, $MnO_2$), and (211, $Al_2O_3$) diffraction planes, respectively. The corresponding HRTEM of the nanocomposite, as depicted in FIG. 2C, shows a plane spacing of 0.242 nm and 0.20 nm related to (311), and (400) planes of spinel, and 0.22 nm related to (200) plane of $MnO_2$, characterizing the heterostructure formation. The fast Fourier transform (FFT) and inverse fast Fourier transform (IFFT) measurements, as depicted in FIGS. 2D and 2E, show a 'd' value of 0.34 nm given to g-$C_3N_4$@$MnO_2$/$MgAl_2O_4$ nanocomposite, signifying the lattice spacing of (002), indicating the development of spinel structure.

According to the present disclosure, the cells may be grown on RPMI-1640 medium supplemented with 10% inactivated fetal calf serum and 50 g/mL gentamycin. The cells may be maintained at 37° C. in a humidified atmosphere with 5% $CO_2$ and were sub-cultured two to three times a week.

For antitumor assays, the tumor cell lines were suspended in medium at concentration $5 \times 10^4$ cell/well in 96-well tissue culture plates (Corning®), followed by incubation for 24 hours. Furthermore, the tested compounds were added into 96-well plates (three replicates) to achieve ten concentrations for each compound. Six vehicle controls with media were run for each 96-well plate as a control. After incubating for 24 hours, the numbers of viable cells were determined by the 3-(4,5-dimethylthiazol-2-yl)-2,5-diphenyltetrazolium bromide (MTT) test. Moreover, the media was removed from the 96-well plate and replaced with 100 microliters (μL) of fresh culture RPMI 1640 medium without phenol red, followed by 10 μL of the 12 millimolar (mM) MTT stock solution (5 mg of MTT in 1 mL of PBS) to each well including the untreated controls. The 96-well plates were then incubated at 37° C. and 5% $CO_2$ for 4 hours. An 85 μL aliquot of the media was removed from the wells, and 50 μL of dimethyl sulfoxide (DMSO) was added to each well and mixed thoroughly with a pipette and incubated at 37° C. for 10 minutes. In addition, in order to determine the number of viable cells, optical density was measured at 590 nm with a microplate reader (SunRise, TECAN, Inc, USA). The percentage viability was calculated using the following expression, $$\left(\frac{ODt}{ODc}\right) \times 100\%$$

where 'ODt' is the mean optical density of wells treated with the tested sample and 'ODc' is the mean optical density of untreated cells. The relation between surviving cells and drug concentration is plotted to get the survival curve of each tumor cell line after treatment with the specified compound. The 50% inhibitory concentration ($IC_{50}$) required to cause toxic effects in 50% of intact cells was estimated from graphic plots of the dose-response curve for each concentration using GraphPad Prism software (San Diego, CA).

Figure 3:
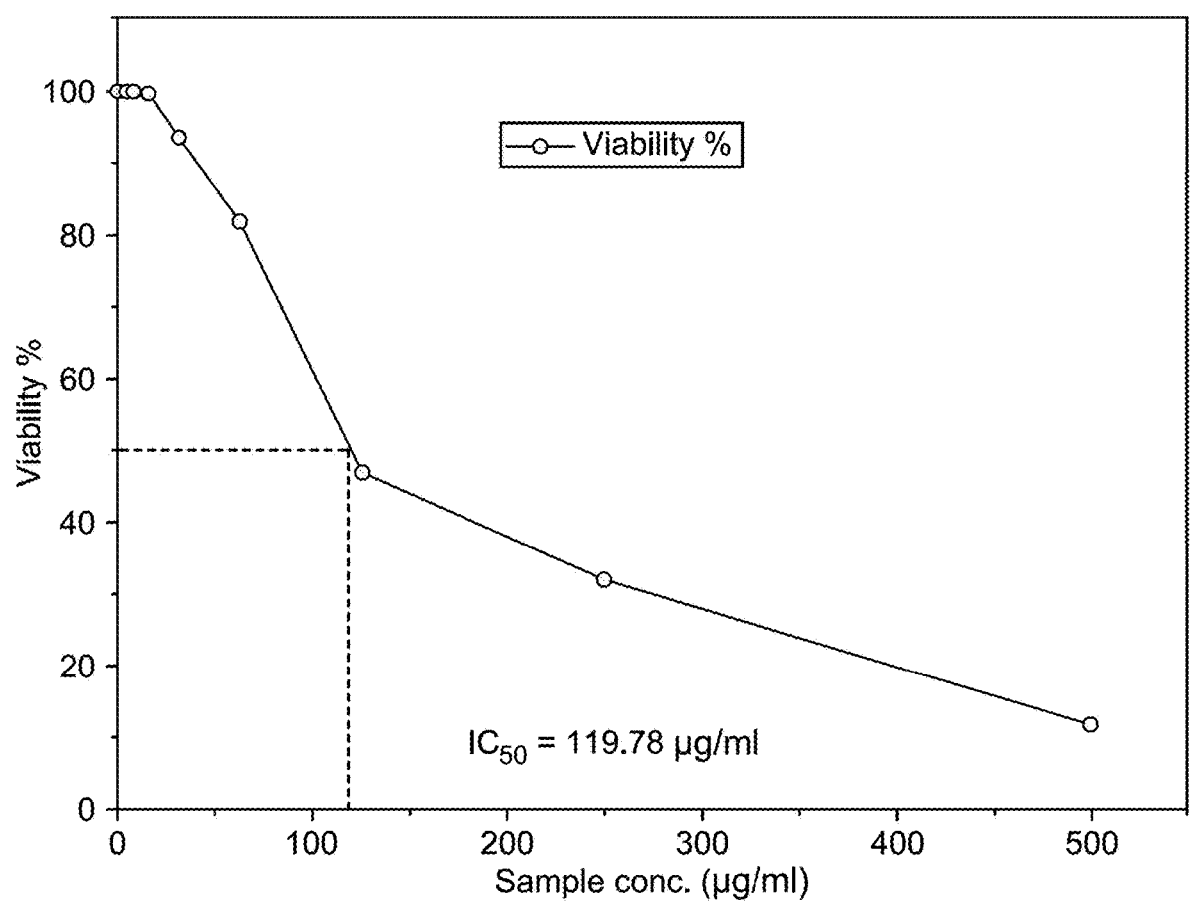
FIG. 3 is a graph depicting nitrogen adsorption-desorption isotherm of an inventive g-$C_3N_4$@$MnO_2$/$MgAl_2O_4$ nanocomposite.

An in-vitro investigation was conducted for the g-$C_3N_4$@$MnO_2$/$MgAl_2O_4$ against human hepatocellular carcinoma (HepG-2) and human breast carcinoma cell lines (MCF-7). A concentration range of 3.0 μg/mL to 500 μg/mL of the g-$C_3N_4$@$MnO_2$/$MgAl_2O_4$ nanocomposite was used. The obtained results against the MCF-7 cell line are illustrated in FIG. 3. The cell viability of the MCF-7 cell started declining with only 15.6 μg/mL g-$C_3N_4$@$MnO_2$/$MgAl_2O_4$ dose. The $IC_{50}$ was 119.78 μg/mL, and the maximum dose of about 500 μg/mL showed an 88.1% inhibition of the MCF-7 cancer cells.

Figure 4:
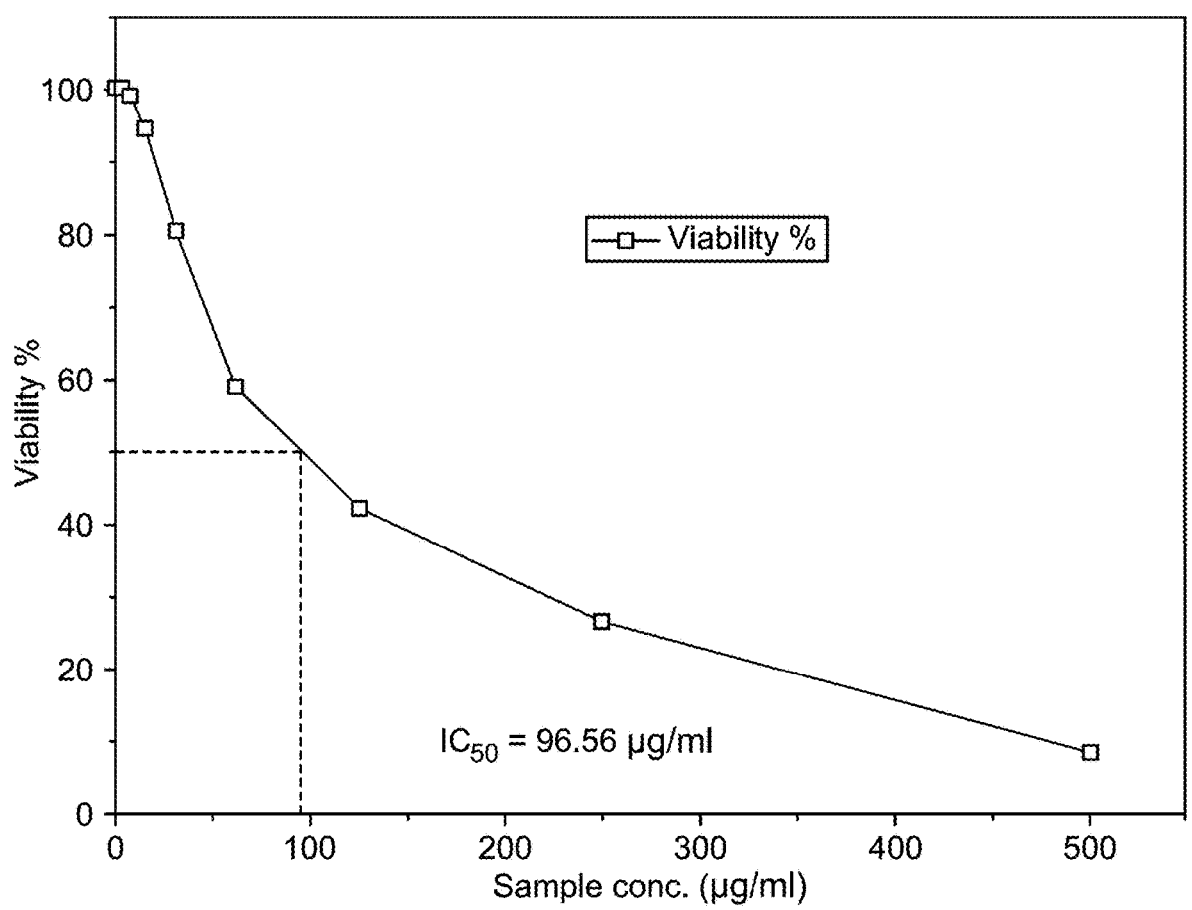
FIG. 4 is a graph depicting the pore size distribution of an inventive g-$C_3N_4$@$MnO_2$/$MgAl_2O_4$ nanocomposite.

Furthermore, the exact concentration range at 3.0 μg/mL to 500 μg/mL of the g-$C_3N_4$@$MnO_2$/$MgAl_2O_4$ nanocomposite was applied against the HepG-2 cell line, and the obtained results against the HepG-2 cell line are illustrated in FIG. 4. The cell viability of the HepG-2 cell started declining with only 7.8 μg/mL g-$C_3N_4$@$MnO_2$/$MgAl_2O_4$ dose. The $IC_{50}$ was 96.5 μg/mL, and the maximum dose of about 500 μg/mL showed a 93.1% inhibition of the HepG-2 cancer cells.

Numerous modifications and variations of the present disclosure are possible in light of the above teachings. It is therefore to be understood that within the scope of the appended claims, the invention may be practiced otherwise than as specifically described herein.

The invention claimed is:

1. A method of inhibiting cancer cell viability, the method comprising:
contacting cancer cells and a nanocomposite comprising graphitic $C_3N_4$, $MnO_2$, and $MgAl_2O_4$ in a mass relationship to each other in a range of from 5 to 15:2 to 7:75 to 95, the nanocomposite being at a concentration in a range of from 10.0 to 500 μg/mL, thereby inhibiting the growth of the cancer cells by at least 85%.

2. The method of claim 1, wherein the average pore distribution of the nanocomposite is unimodal, and
wherein a BET specific surface area of the nanocomposite is in a range of from 16.2 to 20.2 $m^2$/g, and/or
wherein an average pore diameter of the nanocomposite, according to Barrett-Joyner-Halenda (BJH) measurement method, is in a range of from 5 to 15 nm, and/or
wherein an average pore volume of the nanocomposite, according to the BJH measurement method, is in a range of from 0.025 to 0.075 $cm^3$/g.

3. The method of claim 1, wherein the nanocomposite has a (220) spinel interplanar spacing in a range of from 0.258 to 0.338 nm, (400) spinel interplanar spacing in a range of from 0.165 to 0.245 nm, (002) $MnO_2$ interplanar spacing in a range of from 0.106 to 0.186 nm, and (211) $Al_2O_3$ interplanar spacing in a range of from 0.093 to 0.173 nm, according to selected area diffraction.

4. The method of claim 1, wherein the mass relationship of the nanocomposite is in a range of from 9 to 11:4 to 6:84 to 86,
wherein the nanocomposite has a (220) spinel interplanar spacing of 0.298±2% nm, (400) spinel interplanar spacing of 0.205=2% nm, (002) $MnO_2$ interplanar spacing of 0.146±2% nm, and (211) $Al_2O_3$ interplanar spacing of 0.133±2% nm, according to selected area diffraction,
wherein an XRD spectrum of the nanocomposite under Cu-filtered CuKα radiation 1.5418 Å powered at 45 kV and 10 mA has 2θ peaks of
an $MnO_2$ pyrolusite phase at 28.4±1, 40.5±1, 44.9±1, 56.0±1, 66.4±1, and 79.1±1°,
an $MgAl_2O_4$ spinel phase at 19.1±1, 31.3±1, 44.8±1, 56.1±1, 59.5±1, 74.09±1, 78.1±1°,
an MgO cubic phase at 42.8±1, 62.2±1, and 74.6±1°,
an $Al_2O_3$ phase at 31.3±1, 34.3±1, and 61.6±1°,
g-$C_3N_4$-related diffractions at 18.8±1, 28.2±1, 35.5±1, 40.7±1, 44.6±1, and 73.7±1°, and
wherein no more than 5% relative intensity of any other phase is detected in the XRD spectrum.

5. The method of claim 1, wherein the cancer cells are HepG-2 human hepatocellular carcinoma cells and the concentration of the nanocomposite in the contacting is in a range of from 75 to 350 μg/mL, or
wherein the cancer cells are MCF-7 human breast carcinoma cancer cells and the concentration of the nanocomposite is in a range of from 100 to 450 μg/mL.

6. The method of claim 1, wherein the nanocomposite has no more than 0.1 parts, individually, of thiol, amine, carboxylate, and hydroxyl functionalization per 100 $MnO_2$ units, relative to a total metal oxide weight.

7. The method of claim 1, wherein the nanocomposite comprises no more than 1 wt. %, individually, of $TiO_2$, $Ti_2AlN$, $Fe_3O_4$, AlN, ZnO, and $SiO_2$, relative to a total metal oxide weight.

8. The method of claim 1, wherein the nanocomposite comprises no more than 1 atoms of Ce, relative to 100 atom of Mn.

9. The method of claim 1, wherein carbon materials in the nanocomposite comprise no more than 1 wt. %, individually, carbon nanotubes and carbon dots, relative to total nanocomposite weight.

10. The method of claim 1, wherein the nanocomposite no more than 1 wt. % AgBr, relative to a total metal oxide weight, and
wherein the nanocomposite no more than 1 wt. % tungsten oxide, relative to a total nanocomposite weight.

11. The method of claim 1, wherein the nanocomposite comprises no more than 1 wt. % CuS, relative to total nanocomposite weight.

12. The method of claim 1, wherein the nanocomposite comprises no more than 1 wt. %, individually, CuO, aluminosilicate, and $WO_3$, relative to total nanocomposite weight.

13. The method of claim 1, wherein the nanocomposite comprises no more than 1 wt. %, individually, elemental state Co and Fe, relative to total nanocomposite weight.

14. The method of claim 1, wherein the nanocomposite comprises no more than 0.1 wt. % of any noble metal, relative to total nanocomposite weight.

15. The method of claim 1, wherein the nanocomposite comprises no more than 10 wt. % MgO, relative to a total metal oxide weight, and
  wherein the nanocomposite comprises no clay.

16. The method of claim 1, wherein the nanocomposite obtained comprises no more than 1 wt. % carbonaceous material besides the graphitic carbon nitride,
  wherein the graphitic $C_3N_4$ is not nitrogen deficient, and
  wherein carbon materials in the nanocomposite comprise no more than 0.01 wt. % nanotubes and no nanorods, relative to total nanocomposite weight.

17. The method of claim 1, wherein the nanocomposite comprises no more than 10 wt. % $Mn_3O_4$, relative to total manganese oxide weight, and
  wherein the nanocomposite comprises no more than 1 wt. % V-doped ZnO, relative to total nanocomposite weight.

18. The method of claim 1, wherein, relative to a total metal oxide weight, the nanocomposite comprises no more than 1 wt. %, individually, of $K_2Ti_8O_{17}$, $Al_2O_3$, ZnO, $Fe_3O_4$, $CeFeO_3$, $GdFeO_3$, $LaFeO_3$, $BaTiO_3$, $CaTiO_3$, $SrTiO_3$, $CaZrO_3$, $PbTiO_3$, $Mg_{1-x}Ni_xFe_2O_4$ x=0.0, 0.6, 1.0, Ag, $CoFe_2O_4$, $CuFe_2O_4$, $MnFe_2O_4$, $NiFe_2O_4$, $ZnFe_2O_4$, $Cu_{1-x}Cd_xFe_2O_4$, $Zn_{0.7}Ni_{0.15}Cu_{0.15}Fe_2O_4$, $Zn_{0.3}Ni_{0.7-x}Co_xFe_2O_4$ $0 \leq x \leq 0.7$, $Mn_{0.1}Mg_{0.2}Y_{0.7}Fe_2O_4$, wherein Y is Co, Ni or Zn $LaCo_{0.5}Fe_{0.5}O_3$, $Mg_{0.1}$—$Co_{0.9}Fe_2O_4$, $Gd_2FeCrO_6$, $KTaO_3$, $NaTaO_3$, $NaNbO_3$, $KNbO_3$, $Pr_2Ti_2O_7$, $SiO_2$, $TiO_2$, ZnS, $Bi_4O_5I_2$, $SrFe_{0.5}Ta_{0.5}O_3$, $NaNbO_3$, and $LaFeO_3$.

19. The method of claim 1, wherein the graphitic $C_3N_4$ in the nanocomposite consists essentially of sheet morphologies, and/or
  wherein the graphitic $C_3N_4$ in the nanocomposite comprises no more than inevitable traces of boron.

20. The method of claim 1, wherein the nanocomposite comprises no more than 10 wt. %, individually, relative to total metal content, of any of Zn, Ce, Gd, La, Ba, Ti, Ca, Sr, Zr, Pb, Ni, Ag, Au, Co, Cu, Mn, Cd, W, Ta, Nb, Pr, and Bi, and
  wherein the nanocomposite comprises no more than 1 wt. %, individually, relative to total carrier weight, of $SiO_2$, $TiO_2$, ZnO, and ZnS.

* * * * *